United States Patent [19]

Sams et al.

[11] Patent Number: 6,110,730

[45] Date of Patent: Aug. 29, 2000

[54] WHOLE BLOOD CELL STAINING DEVICE

[75] Inventors: Clarence F. Sams, El Lago; Vaughan L. Clift, Houston; Kelly E. McDonald, League City, all of Tex.

[73] Assignee: The United States of America as represented by the Administrator of the National Aeronautics and Space Administration, Washington, D.C.

[21] Appl. No.: 08/678,361

[22] Filed: Jun. 26, 1996

[51] Int. Cl.$^7$ ..................................................... C12M 1/00
[52] U.S. Cl. ......................................................... 435/283.1
[58] Field of Search ............................... 604/403; 422/50, 422/56, 57, 68.1, 102, 97; 436/518, 520–522

[56] References Cited

U.S. PATENT DOCUMENTS

| | | | |
|---|---|---|---|
| 3,701,434 | 10/1972 | Moore | 210/477 |
| 4,066,084 | 1/1978 | Tillander | 128/327 |
| 4,657,869 | 4/1987 | Richards et al. | 435/287 |
| 4,776,843 | 10/1988 | Martinez et al. | 604/86 |
| 4,850,952 | 7/1989 | Figdor et al. | 494/37 |
| 5,008,083 | 4/1991 | Dickie et al. | 422/101 |
| 5,024,238 | 6/1991 | Guirguis | 128/771 |
| 5,192,503 | 3/1993 | McGrath et al. | 422/57 |
| 5,275,057 | 1/1994 | Alexander | 73/799 |
| 5,364,591 | 11/1994 | Green et al. | 422/58 |
| 5,407,642 | 4/1995 | Lord | 422/122 |
| 5,437,635 | 8/1995 | Fields et al. | 604/65 |
| 5,449,622 | 9/1995 | Yabe et al. | 436/63 |
| 5,501,841 | 3/1996 | Lee et al. | 422/101 |

FOREIGN PATENT DOCUMENTS

PCT/US95/05982 of 1995 WIPO .

*Primary Examiner*—Laurie Scheiner
*Assistant Examiner*—J. S. Parkin
*Attorney, Agent, or Firm*—Hardie R. Barr

[57] ABSTRACT

An apparatus and method for using the apparatus for staining particular cell markers is disclosed. The apparatus includes a flexible tube that is reversibly pinched into compartments with one or more clamps. Each compartment of the tube contains a separate reagent and is in selective fluid communication with adjoining compartments.

19 Claims, 2 Drawing Sheets

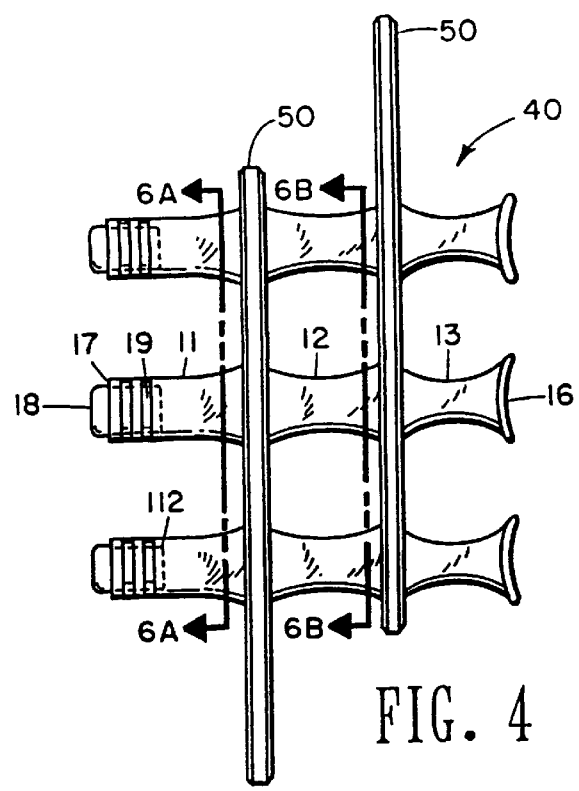
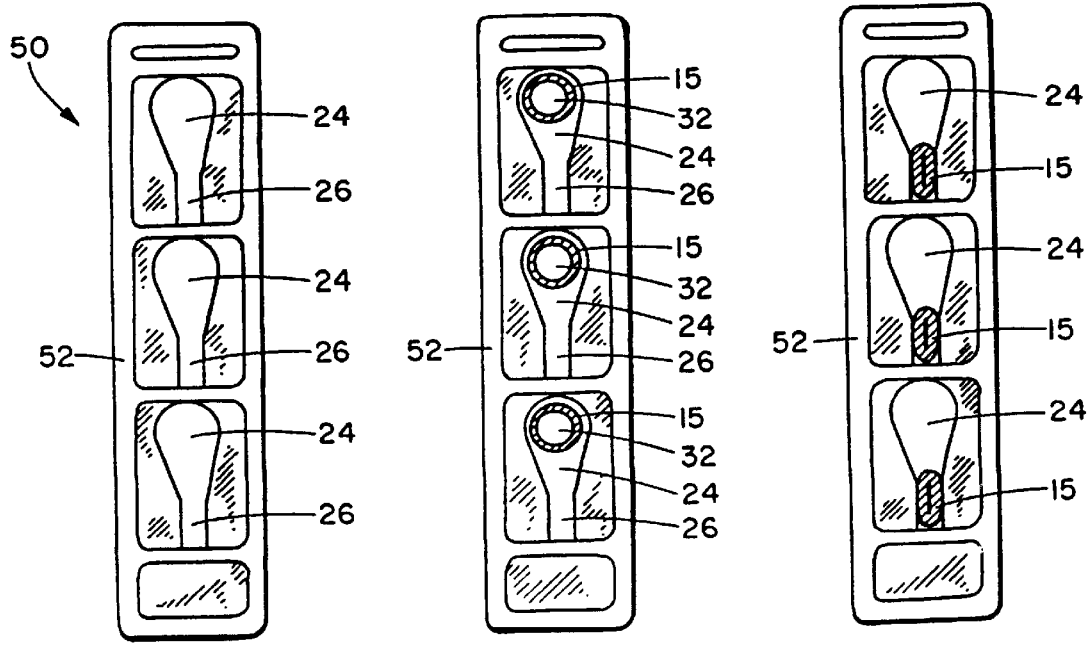
FIG. 4
FIG. 5  FIG. 6A  FIG. 6B

WHOLE BLOOD CELL STAINING DEVICE

ORIGIN OF THE INVENTION

The invention described herein was made in performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

This invention relates to an apparatus and method for staining biological fluids to identify particular cell populations. More particularly, the present invention relates to an apparatus and methods for using the apparatus to react cell populations with specific marker-identifiers and to stabilize the reacted cell populations for transport to a laboratory environment.

BACKGROUND OF THE INVENTION

Biological samples will often contain different types of cells having particular characteristics. Variations in the type of cells or in the characteristics of cells found in biological fluids has been used to diagnose disease and in developing therapeutic protocols. Biological fluids are typically collected and immediately shipped to a laboratory that has the equipment and personnel to process the fluid and determine the presence or absence of particular cell populations in those fluids. A cell population is a collection of cells that may be identified and grouped together because they all express a common cell marker, or molecule that is associated with a type of cell or a characteristic of a cell. However, one of the difficulties in working with living cells is that the cells must be analyzed while they are fresh or they may give spurious results. This can be very difficult when the samples are procured in areas that are difficult or impossible to reach within a short period of time such as certain rural areas, third world countries, and outer space. In fact, biological sample analysis is often foregone because the samples cannot be transported to a laboratory in a timely manner.

One of the most commonly studied biological fluids in blood. The peripheral blood of a normal subject contains red blood cells, also known as erythrocytes, and five major classes of mature white cells. These five classes are known as neutrophils, eosinophils, monocytes, lymphocytes, and basophils. Each type of mature blood cell performs specialized functions necessary in maintaining the homeostasis of the host. The concentration of each class of peripheral blood cells is tightly regulated and monitored by a dynamic process involving a variety of factors present in the microenvironment of the bone marrow.

Under certain disease conditions and therapeutic protocols, the bone marrow may release either an increased or decreased number of certain classes of white cells. Under other conditions and therapeutic protocols, normal regulation of the number of peripheral blood cells released from the bone marrow is perturbed and an uncontrolled number of immature white or red cells are released to the peripheral blood. Therefore, monitoring the concentration of the five normal classes of white cells and identifying the subpopulations of these five normal classes of white cells has become an important diagnostic tool for physicians.

Blood cells, particularly the white cells, exhibit known cell markers that can be used to identify the presence or absence of specific populations, or subpopulations, of white blood cells. For example, the detection of specific cell markers can be used in the diagnosis of particular viral infections. White cells that have been infected with a virus will commonly express some of the coat protein of that virus within its cell membrane. In addition, macrophages that have engulfed infected cells will commonly express those viral coat proteins in their cell membranes. Antibodies to viral antigens, as well as, polynucleic acid probes have been developed and used for detecting cells that have been infected with different types of virus, including for example the Epstein Bar virus and the Hepatitis B virus.

The efficacy of therapeutic regimes and a patient's prognosis may also be assessed by quantifying the number of specific cell populations within the blood, or by quantifying a ratio of specific types of cells. For example, the efficacy of a drug protocol in the treatment of AIDS patients is commonly followed by analyzing their ratio of helper/inducer T lymphocytes (identified by their reaction to a CD4 monoclonal antibody) to suppressor/cytotoxic T lymphocytes (identified by their reaction to a CD8 monoclonal antibody). The response of patients to chemotherapy is also commonly followed by determining the cell differential of patients at various times within their treatment protocol.

A variety of other tests, both diagnostic and predictive, have been developed that take advantage of identifying particular cell markers in cell populations. For example, prenuptial screening for genetic traits is commonly done to assist in the genetic counseling of certain couples who desire to get married and have children. Such genetic screening is commonly performed using DNA probes for known sequences that occur in individuals that have or carry particular genetically inherited traits.

In addition, a number of diagnostic tests that include the identification of specific cell populations expressing particular markers are also used to identify and follow epidemics within a particular animal population. For example, just as viral infections of blood cells may be detected in humans with monoclonal antibodies or other marker identifiers, viral infections of animal populations can also be detected using similar techniques (e.g., the feline leukemia virus).

The determination of cell markers and the use of those markers as a tool for identifying specific blood cell populations has increased as science has expanded its knowledge of cell surface components and the characteristics of subpopulations of lymphocytes, monocytes, neutrophils, eosinophils, and basophils. For example, recent advances in cellular immunology and flow cytometry have been utilized to identify and quantify lymphocyte subclasses such as helper T cells and suppressor T cells. Lymphocyte subclassifications have become an important diagnostic tool, particularly in view of the AIDS epidemic.

Conventional lymphocyte subclassification involves the following steps:

(1) the separation of lymphocytes from other peripheral blood cells by density gradient centrifugation;

(2) the reaction of the lymphocytes with fluorochrome-labelled monoclonal antibodies directed to specific lymphocyte surface antigens; and (3) the analysis of lymphocyte-antibody reaction products using flow cytometry.

Recently, techniques have become available that bypass the need for density gradient centrifugation to separate the lymphocytes.

Currently, most cell differentiation and lymphocyte immunophenotyping is being done utilizing flow cytometry. The Q-PREP™ (manufactured by Coulter Cytometry, Hileah, Fla.) represents an automated methodology for preparing and processing whole blood for flow cytometric analysis. The Q-PREP uses fresh whole blood samples and can be programmed to process multiple samples through a variety of mixing, incubating and washing steps. The Q-PREP is a sophisticated instrument that is impractical to operate in non-laboratory environment.

Alternatively, non-automated processing of whole blood has been done in smaller laboratories or basic research laboratories. These techniques and protocols require the manual pipeting of whole blood into solutions of monoclonal antibodies or other cell marker identifiers. After mixing and incubating these samples, a solution is added to lyse the red blood cells present in the whole blood sample and to fix the reacted white cells. Each step of reagent addition or other manipulation of the blood sample decreases the precision of the overall process and introduces an opportunity for error. Furthermore, the manual procedure is time consuming and requires specialized equipment and technically trained personnel that are generally only available in a laboratory environment.

Immunostaining followed by red cell lysis and white cell fixation is the preferred method for providing flow cytometry samples from fresh whole blood. Current flow cytometric methods require that leukocytes be analyzed free from interference by erythrocytes. In the past, this has been accomplished by density gradient separation of the white cells or by red blood cell lysis with several washing steps. However, it has been reported that centrifugal washing may alter the remaining cellular distribution. The newer lysing solutions, such as FacsLyse™ from Becton Dickinson of San Jose, Calif. and Optilyse™ C from AMAC (Immunotech) of Westbrook, Me., separate the red blood cell debris and white cells without centrifugation or washing steps. Immunophenotypic analysis of peripheral blood leukocytes and lymphocytes is facilitated by the use of such erythrolytic reagents.

All of the described procedures require collecting and shipping fresh whole blood samples to reference laboratories and clinical centers for processing and analysis within hours of its collection. These centers and laboratories possess the technical expertise and equipment to process and analyze infectious blood samples. Whenever the expedited analysis of fresh blood samples is not possible (i.e., within a few hours of collection), the laboratory analyzing the samples must verify that the holding time and the conditions that the sample has undergone have not destroyed the specimen integrity by comparing the drawn specimen to comparable fresh specimens. Field samples procured off-site in areas that may be difficult or impossible to reach within a short period of time such as certain rural areas, third world countries, or outer space must either be capable of being rushed to a clinical laboratory for analysis, or the sample and the analysis of that sample must be foregone.

In addition, blood is generally collected in glass tubes having a stoppered top. During transport of the fresh blood sample to the laboratory, there is a chance that the collection tube may break or that the top of the tube may loosen allowing the blood to leak out of the tube.

SUMMARY OF THE INVENTION

The invention contemplates a simple, self-contained apparatus for reacting the cells in biological fluids with cell marker identifiers and stabilizing the reacted sample for transport and further processing. Thus, the invention solves one or more problems with traditional approaches to cell marker identification.

In accordance with a preferred embodiment of one aspect of the invention, a biological fluid processing apparatus is comprised of a unitary, flexible tube having a top end sealed with a septum and a closed bottom end. The tube is separated into compartments using one or more clamps for pinching the tube to form a reversible seal. Each compartment contains a reagent and depending on the reagents selected the apparatus may be used to identify different cell markers according to the method of injecting a biological fluid through the septum into the first compartment and allowing the reagent in the first compartment to react with the biological fluid. Upon completion of the reaction, the clamp pinching the tube is released or removed, thus permitting the reaction product from the first compartment to flow into the second compartment and react with the reagent in the second compartment.

In accordance with a preferred embodiment of the invention, the biological processing apparatus may contain reagents for the determination of immunotypic lymphocyte subpopulations. The apparatus having a first compartment that contains a dehydrated antibody for binding a cell surface antigen of a lymphocyte subpopulation, a second compartment in selective fluid communication with the first compartment that contains a lysing reagent for lysing red cells and fixing white cells, a third compartment in selective fluid communication with the second compartment that contains a terminating reagent for stopping the action of the lysing reagent, and a reversible sealing means for sealing the first compartment from the second compartment and the second compartment from the third compartment.

In accordance with another aspect of the invention, a method for identifying a blood cell population having an antigenic cell marker uses a container having an amount of a dehydrated antibody directed against the antigenic cell marker. A whole blood sample is injected into the container and is allowed to react with the antibody to produce a portion of the blood cell population with the antibody bound to it. The portion of the cell population with antibody bound to it is then measured.

The foregoing has outlined rather broadly several aspects of the present invention in order that the detailed description of the invention that follows may be better understood and thus is not intended to narrow or limit in any manner the appended claims which define the invention. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes as the invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following description taken in conjunction with the accompanying drawings, wherein:

FIG. 4 illustrates a top view of an alternative embodiment of the biological fluid processing apparatus;

FIG. 5 shows a top view of an alternative embodiment of a clamp for use with the biological fluid processing apparatus of FIG. 4;

FIG. 6A shows a cross-section of the biological fluid processing apparatus illustrated in FIG. 4 taken along section 6A—6A of FIG. 4; and FIG. 6B shows a cross section of the biological fluid processing apparatus illustrated in FIG. 4 taken along section 6B—6B of FIG. 4.

Figure 1:
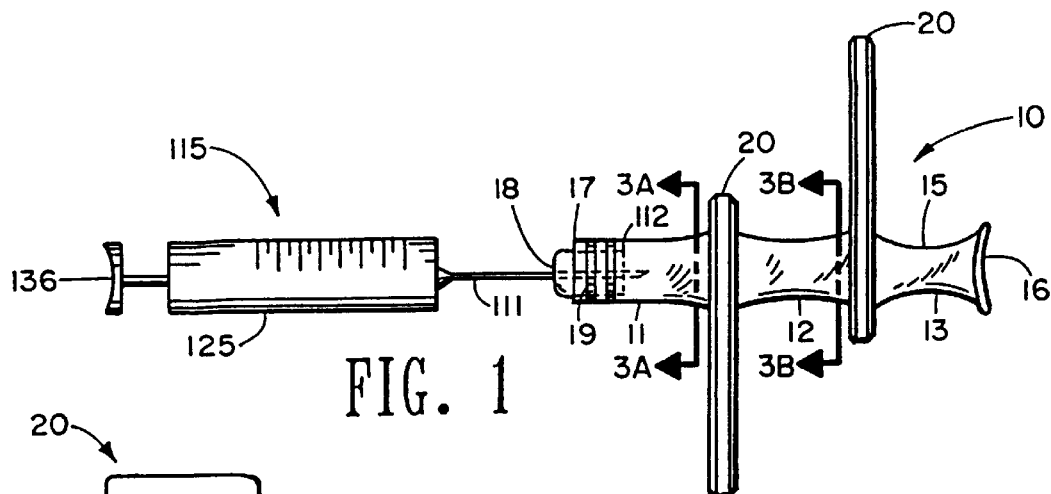
FIG. 1 shows a top view of a biological fluid processing apparatus showing a syringe containing a biological fluid injecting a sample of that fluid into the apparatus.

It is noted, however, that the drawings illustrate preferred embodiments of the invention and are therefore not to be considered limiting of its scope, for the invention may have equivalent embodiments.

DETAILED DESCRIPTION OF THE PREFERRED EMBODIMENT

With reference to the drawings, like reference characters designate like or similar parts throughout the drawings. The figures, or drawings, are not intended to be to scale. For example, purely for the sake of greater clarity in the drawings, wall thickness and spacing are not dimensioned as they actually exist in the assembled embodiment.

Referring to FIG. 1, an apparatus 10 for staining cell markers expressed by cell populations in biological fluids includes a unitary, flexible tube 15 having an open top end 17 sealed with a septum 18 and a closed bottom end 16, tube 15 is formed into a plurality of compartments by pinching the tube in at least one location along its length using one or more clamps 20, or similar devices, to form a reversible seal between the compartments. Each compartment contains an amount of a reagent. The apparatus 10 may be configured to stain any cell population present in any biological fluid including whole blood, urine, amniotic fluid, or cerebrospinal fluid. Once a desired cell population and a specific cell marker for that cell population have been chosen, reagents for identifying the cell marker (a "cell marker identifier") and for stabilizing the cells reacted with the cell marker identifier can be chosen and the apparatus 10 constructed to include the appropriate number of compartments and the selected reagents.

The term "cell marker" refers to a molecular component of a cell that is a member of a specific binding pair (i.e., two different molecules wherein one of the molecules through chemical or physical means specifically binds to the second molecule). The cell marker identifies a cell population that expresses that cell marker either on its surface, in its genome, or other intracellular location. A cell marker is a compound with at least one epitope or binding site that can interact with a specific binding member or cell marker identifier. Cell markers include, but are not limited to, antigenic substances, antibodies, polynucleic acids and combinations thereof which are of interest in diagnostic assays.

The term "cell marker identifier" refers to a specific binding member that will bind to a cell marker with specificity. In addition to antigens and antibodies cell marker identifiers may include lectins, complementary nucleotide sequences, complementary peptide sequences, effector and receptor molecules, enzyme cofactors and enzymes, enzyme inhibitors and enzymes, and the like. Furthermore, types of cell marker identifiers may include variations or derivatives of the specific binding member portion of the cell marker identifier or of the indicator reagent portion of the cell marker identifier. For example, if the cell marker identifier is an antibody, it can be a monoclonal, polyclonal, or chimeric antibody.

The term "indicator reagent" refers to a label that is generally attached to the cell marker identifier that is capable of producing a detectable signal that can be correlated to the presence or amount of the cell marker in the test sample. In general, the indicator reagent is detected or measured with a signal that is produced and detected by visual or instrumental means. Suitable indicator reagents for use in the apparatus 10 include chromogens, catalysts, fluorescent compounds, chemiluminescent compounds, radioactive isotopes, direct visual labels including colloidal metallic and non-metallic particles, and the like. Preferred indicator reagents in the present invention are fluorescent molecules such as fluorescein, phycoerythrin, rhodamine, and the like, along with their derivatives and analogs (or tandem conjugate fluorophores). The selection of a particular indicator reagent is not critical to the apparatus 10, so long as the selected label is capable of generating a detectable signal either by itself or in conjunction with one or more additional substances.

A preferred embodiment of the apparatus 10, illustrated in FIG. 1, is designed to immunophenotype lymphocytes in whole blood samples. Apparatus 10 has a tube 15 that is made of a flexible, preferably plastic-like, material. Although any type of biocompatible flexible material can be used to construct tube 15, a preferred material would be a commercially available Tygon tubing having a thickness of 1/16 to 1/4 inch. Tube 15 has an open end 17 sealed with a septum 18 and a closed end 16 that is preferably heat sealed.

Tube 15 is formed into three compartments by using a first clamp 20 to pinch tube 15 between the top end 17 and the bottom end 16 to form a third compartment 13 and another compartment. A second clamp 20 is then used to pinch tube 15 between the first clamp 20 and the top end 17 of tube 15 to form a first compartment 11 and a second compartment 12. The embodiment of the apparatus 10 for immunotyping lymphocytes will preferably contain one or more fluorochrome labeled antibodies against lymphocyte surface antigens (either in solution or dehydrated) in the first compartment 11, a lysing reagent that will lyse red blood cells and fix the reacted lymphocytes such as Optilyse C in the second compartment 12, and a terminating reagent such as phosphate buffered saline (PBS) to terminate the lysing and fixing reactions in the third compartment 13.

The preferred embodiment of apparatus 10, described above and shown in FIG. 1, is assembled under a laminar flow hood using sterile techniques. A preferred assembly process begins with a tube 15 sterilized by exposure to ethylene oxide and placed in an upright position in a test tube rack with its bottom end 16 down.

A terminating reagent such as sterilized PBS is dispensed into the bottom of tube 15, preferably in an amount approximating 0.5 ml. The terminating reagent may be dispensed into tube 15 using a syringe having a long needle (e.g., a 3½" needle) attached to the syringe. The long needle can be inserted into the lumen 32 of tube 15 for dispensing the PBS into the bottom of the tube 15.

Figure 2A:
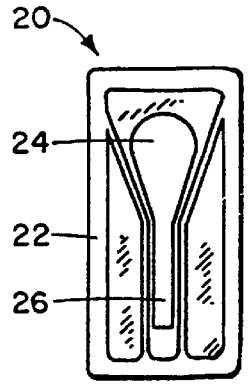
FIG. 2A shows a top view of one embodiment of a clamp for use with the biological fluid processing apparatus of FIG. 1.
Figure 3A:
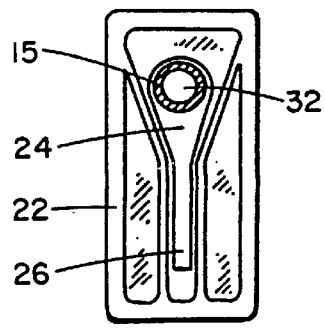
FIG. 3A shows a cross-section of the biological fluid processing apparatus illustrated in FIG. 1 taken along section 3A—3A of FIG. 1.
Figure 3B:
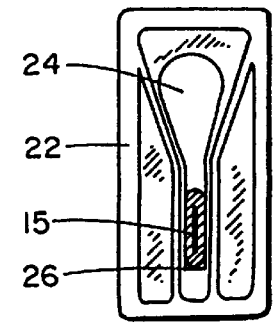
FIG. 3B shows a cross section of the biological fluid processing apparatus illustrated in FIG. 1 taken along section 3B—3B of FIG. 1.

Clamp 20, illustrated in FIG. 2A, is placed over the open end 17 of tube 15. Clamp 20 includes a plate 22 of an inflexible material, such as a solid plastic or metallic material, with an aperture therein. The aperture has a rounded end 24, that is large enough to circumscribe tube 15 with its lumen 32 fully open as seen in FIG. 3A, and a rectangular end 26, that is small enough to force the lumen 32 of tube 15 into a closed position whenever tube 15 is placed into the rectangular end 26 of clamp 20 as shown in FIG. 3B. Tube 15 is placed in the rounded end 24 of clamp 20 and clamp 20 is lowered to a height that is just above the liquid interface provided by the PBS at the bottom of tube 15. Clamp 20 is then moved so that the outside diameter of tube 15 fits within the rectangular end 26 of clamp 20 pinching off tube 15 to create a seal between the third compartment 13 containing the PBS and the second compartment 12.

A syringe containing a lysing reagent is then used to dispense the lysing reagent, preferably about 0.5 ml, into tube 15 just above where the third compartment 13 has been sealed using clamp 20. The rounded end 24 of a second clamp 20 is then placed over open end 17 of tube 15 and the second clamp 20 is lowered to a height just above the interface of the lysing reagent. Once the second clamp 20 is in place it is moved so that the tube 15 is positioned in the rectangular end 26 of clamp 20 forcing shut lumen 32 and sealing the second compartment 12 containing the lysing reagent from the first compartment 11.

Fluorochrome derivatives of monoclonal antibodies (or other cell marker identifiers) are then dispersed into the first compartment 11 of tube 15 just above the second clamp.

The apparatus 10 is then sealed by inserting end 112 of septum 18 into the top end 17 of the apparatus 10. Before inserting end 112 of septum 18 into the top end 17 of tube 15, end 112 is coated with an epoxy or other chemical bonding agent to permanently bond septum 18 to the internal surface of the top end 17 of tube 15. The bond between septum 18 and tube 15 may be reinforced by crimping metal bands 19 around the end of tube 15 where tube 15 overlays end 112 of septum 18.

The assembled apparatus 10 is then stored, preferably at 2–8° C., until use.

In assembling the apparatus 10, a variety of clamps may be used, both manual and automated. Clamp 20 represents one embodiment of the clamp that is easy to use in the field. Clamp 20 has no moving or pivoting parts to break or to jam and does not need electricity to operate. Clamp 20 is highly reliable and is manually operated by sliding the clamp 20 either in the direction that will place tube 15 in the rectangular end 26 thereby pinching the tube 15 and forming two compartments, or in the opposite direction to place tube 15 in the rounded end 24 whereby the lumen 32 will be in an open position and allow fluid communication between the compartments. Clamp 20 can be used multiple times and has no moving parts to wear out.

Figure 2B:
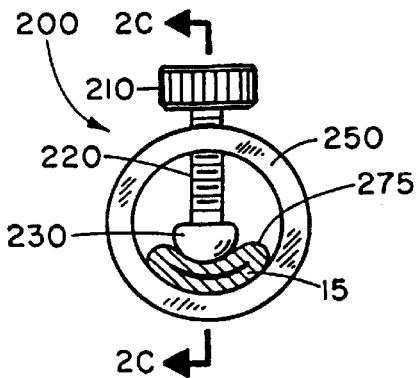
FIG. 2B illustrates a side view of an alternative embodiment for a clamp used in connection with the biological fluid processing apparatus of FIG. 1.
Figure 2C:
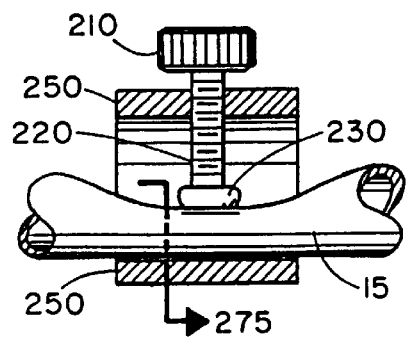
FIG. 2C shows a cross-section of the clamp shown in FIG. 2B taken along section 2C—2C of FIG. 2B.

An alternative embodiment of the clamp is illustrated in FIG. 2B. Clamp 200 has a circular frame 250 that fits around tube 15 and is intersected on one side with a screw 220. The screw 220 has a stem 210 on its top and an engagement end 230 at the bottom of screw 220 located within frame 250. As the stem 210 is turned the distance between the engagement end 230 and the frame 250, on the side opposite to the site where the screw 220 intersects the frame 250, is varied. When tube 15 is placed within frame 250 and the engagement end 230 is lowered, the engagement end 230 will pinch off tube 15 to prevent the flow of liquid through tube 15 at the point where tube 15 is pinched off by engagement end 230. See FIG. 2B. A cross-sectional view of clamp 200 is shown in FIG. 2C showing how the engagement end 230 presses down on the surface of tube 15 until it collapses the lumen 32 of tube 15 as seen in the cross-sectional view 275 of tube 15.

In contrast to clamp 20 and clamp 200, another embodiment of the clamp may be automated using a sensing element to detect certain events such as time and temperature, an amplifier, and a servomotor controlled by a computer program to automate the opening and closing of the clamp.

An alternative embodiment of the apparatus 10 is seen in FIG. 4. This configuration of the apparatus 10 includes a series of tubes 15 essentially parallel to each other. Each tube 15 is assembled as described above; however, the compartments 11, 12, and 13 are formed using clamps that can engage all of the tubes 15 at the same time, as for example, a clamp 50 shown in FIG. 5. Clamp 50 is made of an inflexible plate 52 with a plurality of apertures therein. A tube 15 is inserted into each aperture. The apertures are constructed as described for clamp 20, i.e. each aperture has a rounded end 24 and a rectangular end 26. When tubes 15 are localized in the rounded ends 24 of the apertures the lumens 32 of the tubes 15 are in an open position as illustrated in FIG. 6A, but when the rectangular ends 26 of the apertures are pushed over the tubes 15, the lumens 32 are forced into a closed position as seen in FIG. 6B. By using a clamp 50, or a similar clamp, which will open the junction between two compartments in each of the tubes contained within the clamp simultaneously; one can have a number of tubes processed in exactly the same manner at the same time. This simultaneous processing of multiple tubes 15 not only saves time, but it also provides for comparable samples.

Apart from the various configurations of the apparatus 10 that can be made from different materials, clamps, and the like, the apparatus 10 may include a wide variety of cell marker identifiers, indicator reagents, and the like. This flexibility in the design of the apparatus 10 allows the apparatus 10 to be used in the processing of a large number of cell types.

Current models of multichannel flow cytometers can identify and distinguish three or four different fluorochromes in the same sample. Thus, multiple cell marker identifiers may be used in the same apparatus 10. For example, a preferred embodiment of the apparatus 10 that is designed to determine the ratio of helper T lymphocytes to suppressor T lymphocytes may be made with a fluorescein isothiocyanate (FITC) anti-CD 4 to identify helper T cells, phycoerythrin (PE) anti-CD 8 to identify suppressor T cells, and peridinin chlorophyll protein (PerCP) anti-CD 3 to identify all T cells. Numerous permutations of cell marker identifiers are possible and would be apparent to those skilled in the art, as for example mixtures of antibodies against viral coat proteins or radiolabeled genomic probes for genetically inherited diseases.

Embodiments of apparatus 10 that have multiple tubes such as the one illustrated in FIG. 4 may be designed to be used to study different cell populations of a single individual where each tube in the apparatus 10 will contain a different cell marker identifier, or the multi-tube apparatus 10 may be designed to compare the same cell population of several individuals such that each tube in apparatus 10 will contain the same cell marker identifier. One advantage of the apparatus 10 is that it can be manufactured under stringent quality control standards which minimize the variations in reagent quality and quantity that each sample is processed with.

A major problem that has limited testing samples from distant environments such as third world countries or outer space is that biological samples are inherently unstable. Thus the emphasis to date has been on collecting samples and shipping them directly to a laboratory for analysis as quickly as possible. Since whole blood is only stable for a few hours, it will not survive long term transportation to a laboratory for analysis. For example, the testing of astronaut blood samples in the past has had to be done before the astronauts left earth and upon their return to earth. The apparatus 10 has solved this problem by providing a simple apparatus that can be injected with a whole blood sample and can stain particular cell populations in that sample and preserve the reacted samples during transport In fact, apparatus 10 has been successfully used on one flight in the summer of 1995 to test immunological changes of astronauts in flight.

Cell marker indicators generally require fresh viable cells for optimum results. Yet once the cells have been reacted, they can be fixed or preserved so that the cells are much more stable than in fresh blood. For example, it is generally recommended that blood samples be analyzed within six hours of being drawn; yet processed samples (i.e., where the cells have been reacted with cell marker identifiers, the red blood cells lysed, and the reacted cells fixed) are stable for approximately 96 hours when refrigerated at about 2–6° C.

Another embodiment of the apparatus 10 omits the cell lysis step after reacting the sample with the cell marker identifier. In this embodiment, the sample is reacted with the cell marker identifier and then treated with a fixation/diluent solution. Omission of the lysis step prevents the release of intracellular proteins and provides an extended room temperature stability (of approximately 16 days) for the processed samples. Inclusion of appropriate chemical or radiochemical indicator reagents (e.g., nucleic acid stains) to allow the identification of nucleated cells, will permit the resolution of the white blood cells without the lysis and elimination of the red cells.

By extending the time that the samples can be stored before analysis will allow samples to be drawn in more inaccessible locations, processed using apparatus 10, and shipped to a laboratory environment for further analysis. Therefore, the use of the apparatus 10 may allow scientists to more accurately follow the introduction of new diseases and animal and human epidemics in third world countries.

Another problem that has made sample processing in distant environments such as third world countries or outer space difficult is that some of the cell marker identifiers are not stable at room temperature for more than a few days. For example, a commonly used cell marker identifier is a fluorescent labeled antibody such as a fluorescein isothiocyanate derivative of an anti-CD 19 (FITC-CD19) which will specifically identify B lymphocytes. Solubilized FITC-CD 19 is only stable for two to three days and for a maximum of seven days. The instability of these reagents makes it extremely difficult to ship and/or store the reagents for use in generally inaccessible environments.

A solution to the instability of these cell marker identifiers has been to dehydrate the cell marker identifiers. By dehydrating the FITC-CD 19 either before or after adding it to the first compartment 11 of the apparatus 10, the cell marker identifier is stable for up to 90 days. For example, the stability of the dehydrated FITC-CD19 has been tested by preparing a number of vials with twenty microliter aliquots of FITC-CD 19 antibody therein. Each vial was dried under a nitrogen stream until the FITC-CD 19 was dehydrated. The vials were then capped, stored at room temperature, and tested for B lymphocyte binding using a flow cytometer.

At different time points after the vials were prepared, four vials were tested to ensure the integrity and reactivity of the dehydrated antibody. The vials were tested by adding 0.1 ml of whole blood to the vials, mixing the vials, and incubating the vials in the dark for 30 min. Then 0.5 ml of lysing reagent (Optilyse C) was added to each vial. The vials were mixed for 2–3 seconds and incubated in the dark for 15 min to 2 hr. Next 0.5 ml of PBS was added to each vial and the vial was mixed again. The PBS stopped the lysing process and the vial was then stored in the refrigerator overnight.

The next morning, 3 ml of cold PBS containing azide was added to the blood samples. The vials were then centrifuged at 2000 rpm for 10 min at 4° C. The supernatant was aspirated off and the cell pellet was resuspended and analyzed using a Coulter flow cytometer. The mean value of the flow cytometer peak channel value for the four vials tested on each of the test days remained at 4 or above through day 90, the last time point tested. Four vials were tested on day 14, day 28, day 35, day 48, day 70, and day 90 and each sample gave comparable results to using solubilized fresh FITC-CD 19. These results demonstrate that when the apparatus 10 is prepared using dehydrated fluorescent antibody reagents as cell marker identifiers, that the apparatus 10 is stable at room temperature for at least 90 days. The increased stability of the apparatus 10 at room temperature will substantially expand the use of the apparatus 10 to longer space flights and for inaccessible rural and third world blood sample analysis.

The apparatus 10 represents a very simple and useful apparatus that can be used to process and stain particular cell populations in the home environment, a rural environment, or a space environment. A preferred embodiment of the apparatus 10 is self-contained, small enough to be handheld, and does not require electricity or any equipment to use the apparatus. The apparatus 10 is made to be handled and transported without fear of its breaking or leaking.

The apparatus 10 is simple to use and can be used by unskilled personnel without access to electricity or equipment. All that is required to prepare blood samples for flow cytometric analysis is to inject a small amount of a field sample, such as fresh whole blood, into the first compartment 11 of the apparatus 10 and then to time the various steps of removing the clamps, mixing the samples, and incubating the samples.

The exact method of using the apparatus 10 will depend upon the cell population to be identified, the cell marker identifier being used, and the configuration of the apparatus 10. Basically biological samples are processed in the apparatus 10 in a similar manner to whole blood. The general method for using apparatus 10 to process whole blood is described below.

Peripheral blood is obtained using an aseptic venipuncture technique based on the National Committee for Clinical Laboratory Standards Publication H3-A2, *Procedures for the Collection of Diagnostic Blood Specimens by Venipuncture*. The collected peripheral blood is mixed with an anticoagulant, preferably a salt of ethylenediaminetetraacetate (EDTA), or other anticoagulant such as heparin. All blood specimens should be treated as if they are infectious.

The anticoagulated blood, preferably about 0.1 ml, is injected into the first compartment 11 of tube 15 with syringe 115. To inject the blood a syringe needle 111 is inserted through septum 18 and plunger 136 is pushed towards the apparatus 10 forcing the blood from the syringe barrel 125 into the first compartment 11 of tube 15. The whole blood is mixed with the preparation of cell marker identifier(s) present in the first compartment 11 by gently shaking the apparatus 10 for approximately 10 seconds. The apparatus 10 is then set aside at room temperature for about 30 to 60 minutes to allow the cell marker identifier(s) to bind to the cell marker(s) of the cell population to be identified.

Once the cell marker identifier(s) has been allowed to react with the whole blood, the top clamp 20 is released or removed and the reacted whole blood is allowed to flow into the second compartment 12. The reacted whole blood is then mixed with the lysing reagent in the second compartment 12 by gently shaking the apparatus 10 for about 15 seconds. The apparatus 10 is then set aside at ambient temperature for 20 to 120 minutes to allow the lysing reagent to lyse the red blood cells and to fix the reacted cell population. After the reacted blood cells have incubated with the lysing reagent, the second clamp 20 is released or removed allowing all of the liquid in the second compartment 12 to flow into the third compartment 13. Upon the transfer of the mixture from the second compartment 12 into the third compartment 13, the apparatus 10 is mixed by shaking the apparatus gently for approximately 15 seconds. The entire apparatus with its processed blood can then be stored at 2–6° C. for up to 96 hours without significant changes in the resulting profile of the reacted cells derived from flow cytometric analysis.

As mentioned before, certain configurations of apparatus 10 that omit the lysis step may give processed samples that are stable at room temperature for approximately 16 days.

While preferred embodiments of the invention have been shown and described, it will be apparent to those skilled in the art that the conception and the specific embodiments disclosed herein may be readily utilized as a basis for modifying or designing other apparatuses for carrying out the same purpose as the present invention. It should also be realized by those skilled in the art that such equivalent constructions do not depart from the spirit and scope of the invention as set forth in the appended claims.

What is claimed is:

1. An apparatus for processing biological fluids, said apparatus comprising:
   a flexible tube, said tube having an open top end and a closed bottom end;
   a clamp for reversibly pinching said tube between the top end and the bottom end thereby forming a first and a second compartment having a seal therebetween for preventing fluid communication between said first and said second compartment;
   a first reagent localized in said first compartment;
   a second reagent localized in said second compartment; and
   means for injecting a biological fluid into said first compartment, said injecting means attached to the top end.

2. The apparatus of claim 1, further comprising a second clamp for pinching the tube between the first clamp and the bottom end of the tube to thereby create a third compartment having a seal between said second and said third compartment for preventing fluid communication between said second and said third compartment.

3. The apparatus of claim 2, further comprising a third reagent in said third compartment.

4. The apparatus of claim 1, wherein said first reagent is a cell marker identifier.

5. The apparatus of claim 3, wherein said first reagent is an antibody, said second reagent is a lysing reagent, and said third reagent is a terminating reagent.

6. The apparatus of claim 1, wherein said first reagent is a plurality of fluorochrome labeled monoclonal antibodies.

7. The apparatus of claim 1, wherein said first reagent is a dehydrated antibody that is stable for thirty-five days at room temperature.

8. The apparatus of claim 1, wherein said clamp comprises a plate having an aperture therein, said aperture has a one end that pinches said tube when said tube is localized in said one end and a second end that does not pinch said tube when said tube is localized in said second end of said aperature.

9. The apparatus of claim 1, further comprising a second tube, said second tube aligned essentially parallel to said first tube wherein when said clamp pinches said first tube said clamp concurrently pinches said second tube to thereby form a first and a second compartment having a seal therebetween for preventing fluid communication between said first and said second compartment of said second tube.

10. The apparatus of claim 9, wherein said second tube has a first reagent in said first compartment of said second tube and a second reagent in said second compartment of said second tube.

11. The apparatus of claim 10, wherein said first reagent of said first tube is a first cell marker identifier and said first reagent of said second tube is a second cell marker identifier.

12. The apparatus of claim 11, wherein said first cell marker identifier is identical to said second cell marker identifier.

13. A method for processing biological fluids, said method comprising the steps of:
   providing a processing apparatus, said apparatus comprising a flexible tube having a sealed top end and a closed bottom end and a clamp for reversibly pinching the tube between the top end and the bottom end forming a first and a second compartment having a seal therebetween for preventing fluid communication between said first and said second compartment, said first and said second compartment each containing a reagent;
   injecting a sample of a biological fluid into said first compartment, whereby said biological fluid reacts with said reagent in said first compartment; and
   releasing said clamp to allow fluid communication between said first and said second compartment, whereby said reacted biological fluid from said first compartment reacts with said reagent in said second compartment.

14. The method of claim 13, wherein said biological fluid is whole blood.

15. The method of claim 13, wherein said reagent of said first compartment is a cell marker identifier.

16. The method of claim 13, wherein said reagent of said first compartment is a dehydrated antibody.

17. An apparatus for staining whole blood for the determination of immunotypic lymphocyte subpopulations, said apparatus comprising:
   a flexible tube having a lumen therein;
   reversible clamping means for
      reversibly pinching said tube to close the lumen thereof to form separate compartments in said tube having seals therebetween, said seals preventing fluid communication between adjacent compartments and for reversing the pinching of said tube to allow fluid communication between adjacent compartments;
   a first compartment in said tube containing an amount of an antibody for binding a cell surface antigen of a lymphocyte subpopulation, the first compartment being in fluid communication with at least one adjacent compartment upon reversing said clamping means;

a second compartment in said tube containing an amount of a lysing reagent for lysing red blood cells and fixing white blood cells in a whole blood sample, the second compartment being in fluid communication with at least one adjacent compartment upon reversing said clamping means; and a third compartment in said tube containing an amount of a terminating reagent for stopping the action of the lysing reagent, the third compartment being in fluid communication with at least one adjacent compartment upon reversing said clamping means.

18. The apparatus of claim 17, wherein said antibody includes a plurality of fluorochrome labeled monoclonal antibodies.

19. The apparatus of claim 17, wherein said antibody is dehydrated.

* * * * *